US00PP14783P3

(12) United States Plant Patent
van der Voort

(10) Patent No.: US PP14,783 P3
(45) Date of Patent: May 11, 2004

(54) LILY PLANT NAMED 'ROUSILLON'

(50) Latin Name: *Lilium l.*
Varietal Denomination: Rousillon

(75) Inventor: Cees A. van der Voort, Katwijk (NL)

(73) Assignee: Vletter & Den Haan Beheer B.V. (NL)

( * ) Notice: Subject to any disclaimer, the term of this patent is extended or adjusted under 35 U.S.C. 154(b) by 0 days.

(21) Appl. No.: 09/521,611

(22) Filed: Mar. 9, 2000

(65) Prior Publication Data

US 2002/0066129 P1 May 30, 2002

(51) Int. Cl.[7] ..... A01H 5/00
(52) U.S. Cl. ..... Plt./315
(58) Field of Search ..... Plt./315

(56) References Cited

U.S. PATENT DOCUMENTS

PP9,201 P * 7/1995 Egger et al. ..... Plt./315

OTHER PUBLICATIONS

UPOV ROM GTITM Computer Database, GTIJOUVIER Retrieval Software, citations for 'Rousillon' 2002/02.*
UPOV–ROM GTITM Computer Database, GTI JOUVE Retrieval Software, citations for 'Rousillon', Aug. 2000.*

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct cultivar of Lily plant named 'Rousillon' characterized by its erect to vertical flowers, intense purple-red color with contrasting orange pollen and stripes, spots and flakes on the inner side of the throat, and vigorous growth.

1 Drawing Sheet

BACKGROUND OF THE INVENTION

The present invention comprises a new and distinct cultivar of lily plant, botanically known as *Lilium l.*, and hereinafter referred to by the cultivar name 'Rousillon'.

'Rousillon' is a product of a planned breeding program which had the objective of creating new lily cultivars having many large erect flowers and vigorous growth.

'Rousillon' was originated from a hybridization made by the inventor in a controlled breeding program in Rijnsburg, the Netherlands in 1992. The male and female parents were unnamed seedlings of *Lilium l.* oriental hybrids. Both parents are proprietary cultivars used in the breeding program.

'Rousillon' was discovered and selected as one flowering plant within the progeny of the stated cross by the inventor, Cees A. van der Voort, in the months of May and June 1992 in a controlled environment in Rijnsburg, the Netherlands.

The first act of asexual reproduction of 'Rousillon' was accomplished when scales were taken from the initial selection in October 1994 in a controlled environment in Rijnsburg, the Netherlands by, or under the supervision of, Cees A. van der Voort. Horticultural examination of selected units initiated in May, 1994 has demonstrated that the combination of characteristics as herein disclosed for 'Rousillon' are firmly fixed and are retained through successive generations of asexual reproduction.

BRIEF DESCRIPTION OF THE INVENTION

The following traits have been repeatedly observed and are determined to be basic characteristics of 'Rousillon' which in combination distinguish this lily as a new and distinct cultivar:

1. large flowers;
2. erect to vertical flowers arranged in a longitudinal axis;
3. red-purple color with contrasting orange pollen and marking and spots on the inner side of the throat; and
4. vigorous growth habit.

'Rousillon' has not been observed under all possible environmental conditions. The phenotype of the new cultivar may vary significantly with variations in environment such as temperature, light intensity, and daylength without any change in genotype. The following observations, measurements, and comparisons describe plants grown in the experimental research station CPRO-DLO, Wageningen, the Netherlands under conditions which approximate those generally used in commercial practice.

Of the many commercial cultivars known to the present inventor, no other cultivars are similar in comparison to 'Rousillon'.

BRIEF DESCRIPTION OF THE DRAWING

The accompanying color photographic illustration shows typical plant and flower characteristics of 'Rousillon', with colors being as true as possible with illustrations of this type.

DETAILED BOTANICAL DESCRIPTION

In the following description, color references are made to The Royal Horticultural Society (R.H.S) Colour Chart. The color values were determined between 12 pm and 2 pm in June 1999 at the experimental research station CPRO-DLO, Wageningen, the Netherlands.

The age of the described plant is between 100–120 days after planting the bulbs. The instant plant was grown between 12/13° C. and 17/18° C. greenhouse. The average daylight during cultivation from April to July was 12–18 hours per day. Fertilizers like Fe and Ca are applied depending on the conditions of the soil in which the bulbs are planted. Average watering rate is 2 times 5 min. per day during the cultivation period. The quantity of irrigation strongly depends on the outside temperatures and light levels.

Origin: Selected crossing from a controlled hybridization program.

Parentage:

*Female parent.*—Unnamed seedling.

*Male parent.*—Unnamed seedling.

Classification:

*Botanical.*—A hybrid of the genus *Lilium l.*

*Commercial.*—Oriental Lily cv. 'Rousillon'.

Plant:

*Form.*—A single stem carrying numerous, alternately arranged leaves.

*Height.*—Short to medium for the mature plant, approximately 70 cm, depending on cultivation conditions.

*Growth habit.*—Vigorous. Growth of the plant to about 105 cm depends on temperatures and on other factors.

*Stem.*—Circular in transverse section; anthocyanin pigmentation present in spots and stripes (RHS 199B); internodal length uniform.

Foliage:

*Quantity.*—Approximately 30–40, depending on cultivation conditions.

*Size of leaf.*—Approximately 8½ cm long and 3½ cm wide, depending on cultivation conditions.

*Shape of leaf.*—Generally ovate.

*Texture.*—Hardly any pubescence.

*Color.*—Light-green.

Bulb:

*Size.*—16 to 18 cm in circumference.

*Color.*—White/pink.

*Leaf apex shape.*—Pointed.

*Leaf base shape.*—Convex.

*Bulb shape.*—Concave.

*Upper surface of the foliage.*—RHS 138A.

*Lower surface of the foliage.*—RHS 138A.

*Gray-shading flower bulb.*—None.

*Bulb color.*—RHS 85D.

Bud:

*Form.*—Tapering like a lancet.

*Size.*—Short in length, depending on cultivation conditions.

*Opening.*—Unfolds normally in standard cultivation conditions.

*Color.*—Reddish-purple, RHS 60C, but more grayish just before opening.

*Tepals.*—Folded, three visible.

*Bud diameter.*—2 cm.

Flower:

*Blooming habit.*—Raceme.

*Size.*—Short to medium, approximately 14 cm in diameter, depending on cultivation conditions.

*Borne.*—Erect to vertical along a longitudinal axis.

*Shape.*—Generally, hexagonal star in form and bowl-shaped in cross-section.

Tepalage:

*Number of tepals.*—6.

*Arrangement.*—Three inner and three outer.

Color:

*Upper surface.*—Reddish-purple, between RHS 60B and RHS 60C.

*Lower surface.*—Reddish-purple, RHS 64B.

*Spotting or marking.*—Dark-purple spots, stripes and flakes are present on the inner side of the throat.

*Pedicel.*—Length: Medium to large, depending on cultivation conditions. Form: Tapering like a lancet.

*Texture.*—Papillose.

*Disease resistance.*—Medium.

*Fragrance.*—Present.

*Lasting quality.*—Excellent.

*Tepal length.*—6–7 cm.

*Tepal width.*—3 cm.

*Tepal (inner and outer) shape.*—Pointed.

*Pedicel length.*—3.5 cm (depending on growing conditions).

*Pedicel diameter.*—2.5 mm.

*Colour of dark spots and markings.*—RHS 64A.

*Pedicels.*—RHS 138C.

*Anther.*—RHS 154C.

*Filament.*—RHS 154D.

*Pollen.*—RHS 28A.

*Pistil.*—RHS 160B.

Reproductive organs:

*Stamens and anthers.*—Arrangements: Anthers form a generally circular pattern at their upper ends. Number: 6. Length: Filaments Medium, depending on cultivation conditions. Filaments Color. Yellowish-green.

*Pollen color.*—Orange-brown.

*Anther color.*—Purplish-red.

*Pistils.*—Yellowish-green.

*Stigma.*—Gray, purplish fading.

*Ovaries.*—Triangular in shape.

The plant spread, at the moment the plant is mature (3 flowers opened after 100–120 days) is 25–35 cm. depending on growing conditions.

The instant plant is not resistant against diseases/pests and moderate susceptible compared to the species as a whole.

The instant plant's fragrance is very strong.

The lastingness of the individual bloom of the instant plant is about 7 days, depending on the environmental conditions.

The cold hardiness of the instant plant is average. The plant can be grown in temperatures from 10–30 degrees Centigrade.

I claim:

1. A new and distinct cultivar of Lily plant named 'Rousillon', as illustrated and described herein.

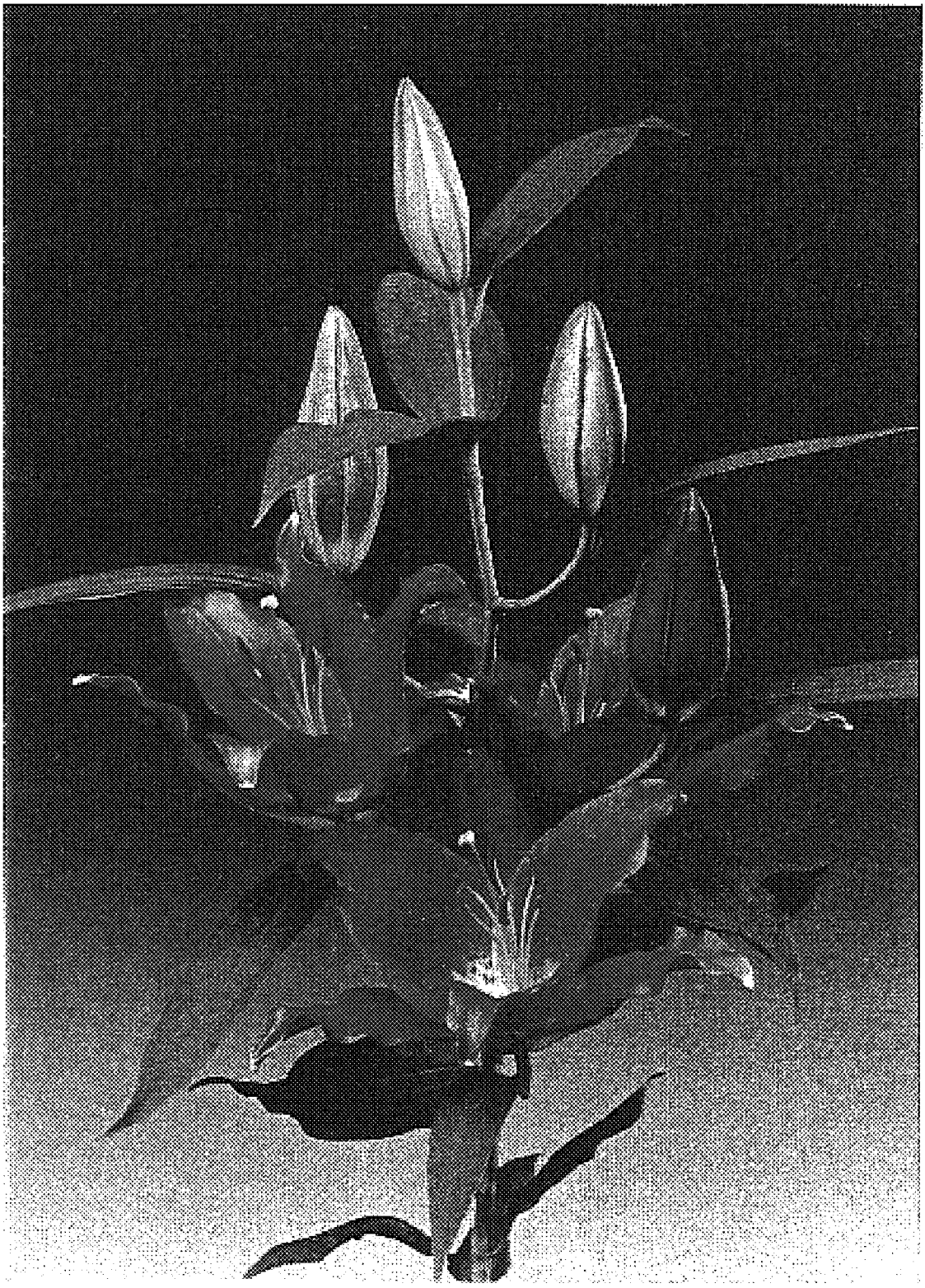

* * * * *